United States Patent [19]
Roth et al.

[11] Patent Number: 5,403,453
[45] Date of Patent: Apr. 4, 1995

[54] METHOD AND APPARATUS FOR GLOW DISCHARGE PLASMA TREATMENT OF POLYMER MATERIALS AT ATMOSPHERIC PRESSURE

[75] Inventors: John R. Roth; Peter P. Tsai; Larry C. Wadsworth; Chaoya Liu; Paul D. Spence, all of Knoxville, Tenn.

[73] Assignee: The University of Tennessee Research Corporation, Knoxville, Tenn.

[21] Appl. No.: 145,349

[22] Filed: Oct. 29, 1993

Related U.S. Application Data

[63] Continuation-in-part of Ser. No. 68,739, May 28, 1993.

[51] Int. Cl.$^6$ .............................................. H05F 3/00
[52] U.S. Cl. ................................................... 204/164
[58] Field of Search ........................................ 204/164

[56] References Cited

FOREIGN PATENT DOCUMENTS

| 0068775 | 1/1983 | European Pat. Off. |
| 0117561 | 9/1984 | European Pat. Off. |
| 200133 | 9/1986 | Japan |
| 62-235339 | 10/1987 | Japan |

OTHER PUBLICATIONS

Authors: Von Engel, A.; Seeliger, R.; & Steenbeck, M. Title: On the Glow Discharge at High Pressure Publication: *Ziet, fur Physik*, vol. 85 (1933) pp. 144–160.

Authors: Wakida, T.; Kawamura, H.; Han, L.; Hwan Kim, K.; Goto, T.; & Takagishi, T. Title: Changes in Surface Properties of Poly(Ethylene Terephthalate) Treated with Low Temperature Plasma: Effect of Pretreatment with Dimethylformamide Publication: *sen-i gakkaishi*, vol. 43, No. 7 (1987).

Authors: Wakida, T.; Kawamura, H.; Song, J. C.; Goto, T.; Takagishi, T. Title: Surface Free Energy Poly-(Ethylene Terephthalate) and Nylon 6 Films Treated with Low Temperature Plasma Publication: *Seni-I Gakkaishi*, vol. 43, No. 7 (1987).

Authors: Kogoma, M.; Kasai, H.; Takahashi, K.; Moriwaki, T. & Okazaki, S. Title: Wettability Control of a Plastic Surface by CF$_4$ Plasma and Its Etching Effect Publication: *J. Phys. D: Appl. Phys.*, vol. 20 (1987).

Authors: Kanazawa, S.; Kogoma, M.; Moriwaki, T.; & Okazaki, S. Title: Stable Glow Plasma at Atmospheric Pressure Publication: *J. Physics D: Appl. Phys.*, vol. 21 (1988) pp. 838–840.

Author: Rakowski, W. Title: Plasma Modification of Wool Under Industrial Conditions Publication: *Melliand Textilberichte*, vol. 70 (1989) pp. 780–785.

Authors: Yokoyama, T.; Kogoma, M.; Moriwaki, T.; & Okazaki, S. Title: The Mechanism of the Stabilisation of Glow Plasma at Atmospheric Pressure Publication: *J. Physics D. App. Phys.*, vol. 23 (1990) pp. 1125–1128.

Authors: Naoki Kanda; Masuhiro Kogoma; Hiroshi Jinno; Hiroshi Uchiyama & Sachiko Okazaki Title: Atmospheric Pressure Glow Plasma and Its Application to Surface Treatment and Film Deposition. Publication: *International Symposium on Plasma Chemistry*, Symposium Proceedings, vol. 3, Bochum, Germany, Aug. 4–9, 1991.

Authors: Liu, C.; Chen, D.; & Roth, J. R. Title: Characteristics of a Steady-State, Low Power Glow Discharge at Atmospheric Pressure Publication: *APS Bulletin*, vol. 37, No. 6 (1992) p. 1563.

Authors: Roth, J. R.; Liu, C.; & Laroussi, M. Title: Experimental Generation of a Steady-State Glow Discharge at Atmospheric Pressure Publication: Paper (List continued on next page.)

*Primary Examiner*—John Niebling
*Assistant Examiner*—Kishor Mayekar
*Attorney, Agent, or Firm*—Weiser & Associates

[57] ABSTRACT

Polymer materials such as film and fabrics, woven, non-woven and meltblown, may be non-destructively surface treated to improve water wettability, wickability, and other characteristics by exposure to a glow discharge plasma sustained at substantially atmospheric pressure in air or modified gas atmospheres comprising helium or argon.

12 Claims, 11 Drawing Sheets

OTHER PUBLICATIONS 5P-21, *Proc. 1992 IEEE International Conference on Plasma Science*, Tampa, Fla., IEEE Catalog No. 92-TH0460-6, ISBN 0-7803 0716-X (1992), pp. 170-171.

Authors: Reitz, H.; Schwarz, R.; Salge, J. G. H. Title: Power Modulation for Dielectric Barrier-Discharges Publication: Paper presented at *Twentieth Power Modulator Symposium*, 1992.

Author: Rakowski, W. Title: Effect and Cost of Plasma Treatment of Polypropylene Melt Blown Webs Publication: *Second Annual TANDEC Conference*, 13-16 Oct., 1992.

Author: Liu, C. Title: Plasma-Related Characteristics of a Steady-State Glow Discharge at Atmospheric Pressure Publication: Presented at the 1993 Sigma XI Graduate Student Paper Competition, The University of Tennessee, Knoxville, Tenn. on Mar. 4, 1993.

Authors: Roth, J. R.; Spence, P. D.; Liu, C. Title: Plasma-Related Characteristics of a Steady-State Glow Discharge at Atmospheric Pressure Publication: Paper 2P-18, *Proc. 1993 IEEE International Conference on Plasma Science*, Vancouver, B. C. IEEE Catalog No. 93-CH3334-0, ISBN 0-7803-1360-7 (1993), p. 129.

Authors: Roth, J. R.; Spence, P. D.; Liu, C. Title: Preliminary Measurements of the Plasma Properties of a One Atmosphere Glow Discharge Plasma Publication: Paper present at 35th Annual Meeting of the APS Division of Plasma Physics, St. Louis, Mo., Nov. 1-5, 1993; *APS Bulletin*, Series II, vol. 38, No. 10 (1993), p. 1901.

METHOD AND APPARATUS FOR GLOW DISCHARGE PLASMA TREATMENT OF POLYMER MATERIALS AT ATMOSPHERIC PRESSURE

This invention was made with government support under Contract No. AFOSR-89-0319 awarded by the U.S. Air Force. The government has certain rights in this invention.

CROSS-REFERENCES TO RELATED APPLICATIONS

This application is a Continuation-In-Part of U.S. patent application Ser. No. 08/068,739, filed May 28, 1993.

FIELD OF INVENTION

The present invention relates to a method and apparatus for modifying the surface properties of organic and inorganic polymer materials such as film and fabric, woven and non-woven.

DESCRIPTION OF THE PRIOR ART

One of the many utilities for meltblown polymer web is as a wet cell battery plate separator. The base polymer compound is impervious to the electrolyte. The meltblown, non-woven fabric structure is ion permeable if the surface thereof is thoroughly wetted by the electrolyte. Unfortunately, this latter requirement of wettability is not an inherent characteristic of most commercial polymers such as nylon, polypropylene, polyethylene and poly(ethylene terephthalate).

Although meltblown webs of these polymers are currently used as battery plate separators, wettability is achieved chemically by means of surfactants. This process not only generates hazardous industrial waste but produces a product of limited utility life.

Wettability is also a desirable property for tissue and cloth used to wipe or clean the body, for surgical sponges, wound dressings, feminine hygiene products and reuseable woven knit fabrics. Similarly, wettability is an important material surface property for printing and laminating.

Some success has been recently achieved by a glow discharge plasma treatment of polymer webs. The term "plasma" usually describes a partially ionized gas composed of ions, electrons and neutral species. This state of matter may be produced by the action of either very high temperatures, or strong direct current (DC) or radio frequency (RF) electric fields. High temperature or "hot" plasmas are represented by celestial light bodies, nuclear explosions and electric arcs. Glow discharge plasmas are produced by free electrons which are energized by an imposed DC or RF electric field and then collide with neutral molecules. These neutral molecule collisions transfer energy to the molecules and form a variety of active species which may include photons, metastables, individual atoms, free radicals, molecular fragments, monomers, electrons and ions. These active species are chemically active and/or capable of physically modifying the surface and may therefore serve as the basis of new surface properties of chemical compounds and property modifications of existing compounds.

Low power plasmas known as dark discharge coronas have been widely used in the surface treatment of thermally sensitive materials such as paper, wool and synthetic polymers such as polyethylene, polypropylene, polyolefin, nylon and poly(ethylene terephthalate). Because of their relatively low energy content, corona discharge plasmas can alter the properties of a material surface without damaging the surface.

Glow discharge plasmas represent another type of relatively low power density plasma useful for non-destructive material surface modification. These glow discharge plasmas can produce useful amounts of visible ultraviolet radiation. Glow discharge plasmas have the additional advantage therefore of producing visible and UV radiation in the simultaneous presence of active species. However, glow discharge plasmas have heretofore been successfully generated typically in low pressure or partial vacuum environments below 10 torr. Several polymer species exposed to low pressure glow discharge plasmas respond with enhanced surface wettability characteristics. However, the chemical/physical mechanisms are not understood and the characteristic is lost upon drying. Rewettability remains elusive.

The generation of low power density plasmas at one atmosphere is not new. Filamentary discharges between parallel plates in air at one atmosphere have been used in Europe to generate ozone in large quantities for the treatment of public water supplies since the late 19th century. Such filamentary discharges, while useful for ozone production, are of limited utility for the surface treatment of materials, since the plasma filaments tend to puncture or treat the surface unevenly.

It is an object of the present invention, therefore, to provide a non-byproduct producing process for enhancing the wettability of meltblown polymer webs and other types of polymeric substrates.

Another object of the invention is to teach a glow discharge plasma process for treating polymer web or film that provides a stable, rewettable product.

Another object of the invention is to provide a method and apparatus for continuously processing a polymer web or film of indefinite length through a glow discharge plasma at atmospheric pressure and standard temperature.

A still further object of the present invention to teach the construction and operating parameters of a glow discharge plasma having operability in an environmental pressure of about one atmosphere or slightly greater.

INVENTION SUMMARY

These and other objects of the invention to be subsequently explained or made apparent are accomplished with an apparatus based upon a pair of electrically insulated metallic plate electrodes which may or may not have a median plate or screen between them. These plates are mounted in face-to-face parallel or uniformly spaced alignment with means for reciprocatory position adjustment up to about 5 cm of separation. Preferably, the plates are water cooled and covered with a dielectric insulation.

A radio frequency power amplifier connected to both plates delivers at least 180 watts of reactive and plasma power at a working voltage of 1 to at least 5 KV rms and at 1 to 100 KHz.

An electric field established between the metallic plate electrodes must be strong enough to electrically break down the gas used, and is much lower for helium and argon than for atmospheric air. The RF frequency must be in the right range, discussed below, since if it is too low, the discharge will not initiate, and if it is too high, the plasma forms filamentary discharges between the plates. Only in a relatively limited frequency band will the atmospheric glow discharge plasma reactor form a uniform plasma without filamentary discharges.

At least in the volume between the plates wherein the plasma is established, a one atmosphere charge of air, nitrous oxide, helium or argon is established and maintained for processing material such as polymer film and web to produce desired surface characteristics such as wettability and re-wettability.

BRIEF DESCRIPTION OF THE DRAWINGS

Relative to the drawings wherein like reference characters designate like or similar elements throughout the several figures of the drawings.

DESCRIPTION OF THE PREFERRED EMBODIMENT

Figure 1:
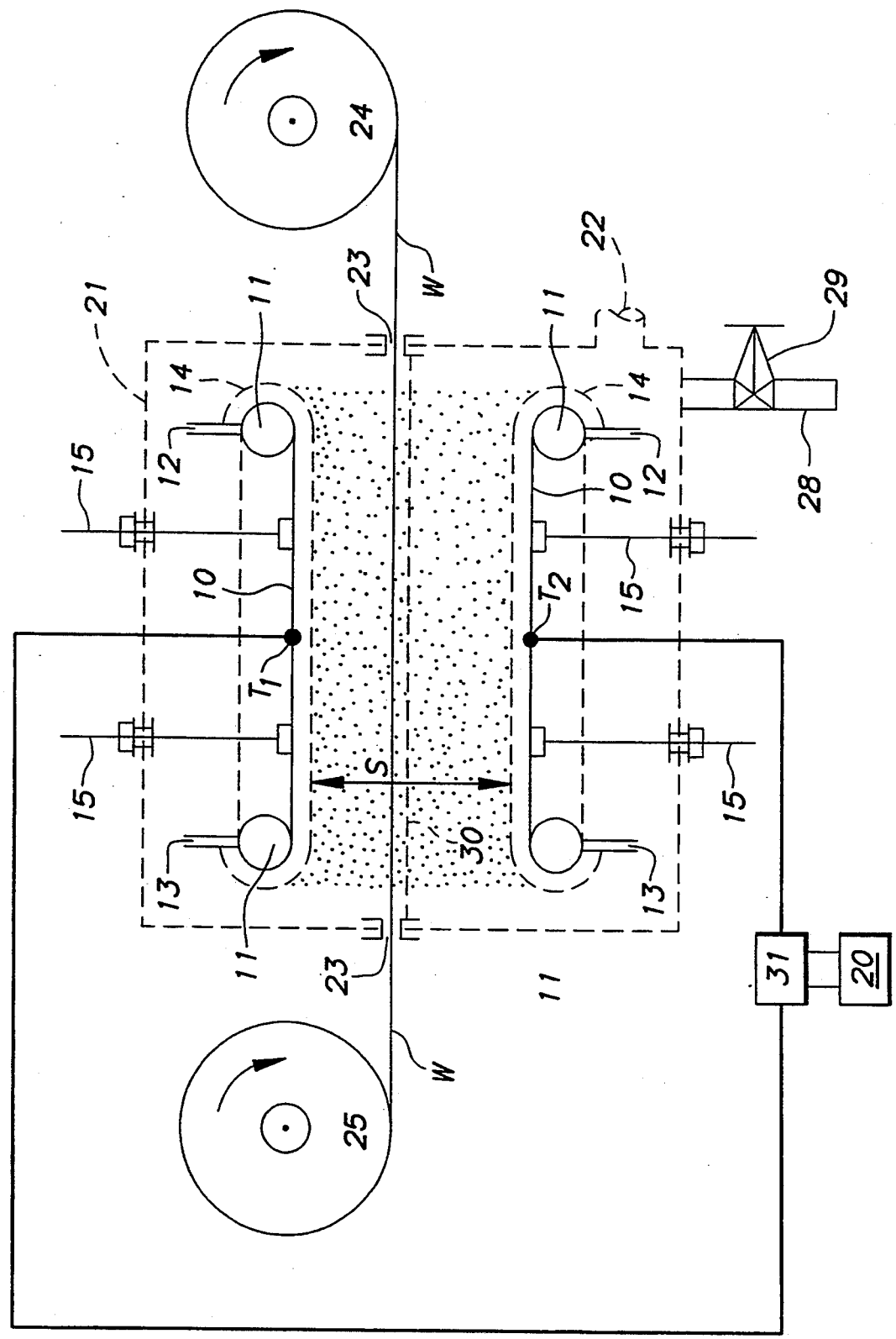
FIG. 1 is a schematic of the present invention component assembly.

Referring to the invention schematic illustrated by FIG. 1, the electrodes 10 are fabricated of copper plate having a representative square plan dimension of 21.6 cm×21.6 cm. Silver soldered to the plates 10 are closed loops 11 of 0.95 cm copper tubing having hose nipples 12 and 13 connected therewith on opposite sides of the closed tubing loop. Not shown are fluid flow conduits connected to the inlet nipples 12 for delivering coolant fluid to the loop 11 and to the outlet nipples 13 for recovering such coolant fluid.

The integral metallic units comprising plates 10 and tubing 11 are covered with a high dielectric insulation material 14.

Preferably, some mechanism should be provided for adjusting the distance s between plates 10 up to about 5 cm separation while maintaining relative parallelism. Such a mechanism is represented schematically in FIG. 1 by the rod adjusters 15 secured to the upper and lower plates 10. This arrangement anticipates a positionally fixed median plate 30.

Although parallelism is used in the context of parallel planes, it should be understood that the terms also comprises non-planar surfaces that are substantially equidistant. Also included are the geometry characteristics of a cylinder having an axis parallel to another cylinder or to a plate.

Energizing the plates 10 is a low impedance, high voltage, R. F. power amplifier 20 having independently variable voltage and frequency capacities over the respective ranges of 1 to at least 5 KV and 1 to 100 KHz. Between the RF power supply 20 and the plates 10 may be an impedance matching network 31, described in greater detail relative to FIG. 2.

Surrounding the plate assembly is an environmental isolation barrier 21 such as a structural enclosure suitable for maintaining a controlled gas atmosphere in the projected plan volume between the plates 10. Inlet port 22 is provided to receive an appropriate gas such as air, helium or argon, mixtures of helium or argon with oxygen or air or a mixture of argon with helium. In any case, gas pressure within the isolation barrier 21 is substantially ambient thereby obviating or reducing the need for gas tight seals. Normally, it is sufficient to maintain a low flow rate of the modified atmospheric pressure gas through the inlet port 22 that is sufficient to equal the leakage rate. Since the pressure within the isolation barrier 21 is essentially the same as that outside the barrier, no great pressure differential drives the leakage rate. A vent conduit 28 controlled by valve 29 is provided as an air escape channel during initial flushing of the enclosure. Thereafter, the valve 29 may be closed for normal operation.

Narrow material flow slits 23 are provided in the isolation barrier 21 to accommodate passage of a material web W between the plates 10 as drawn from a supply reel 24 onto a rewind reel 25. Drive for the reels 24 and 25 is controlled to provide a predetermined residence time between the plates 10 and within the plasma for any given web element.

Figure 2:
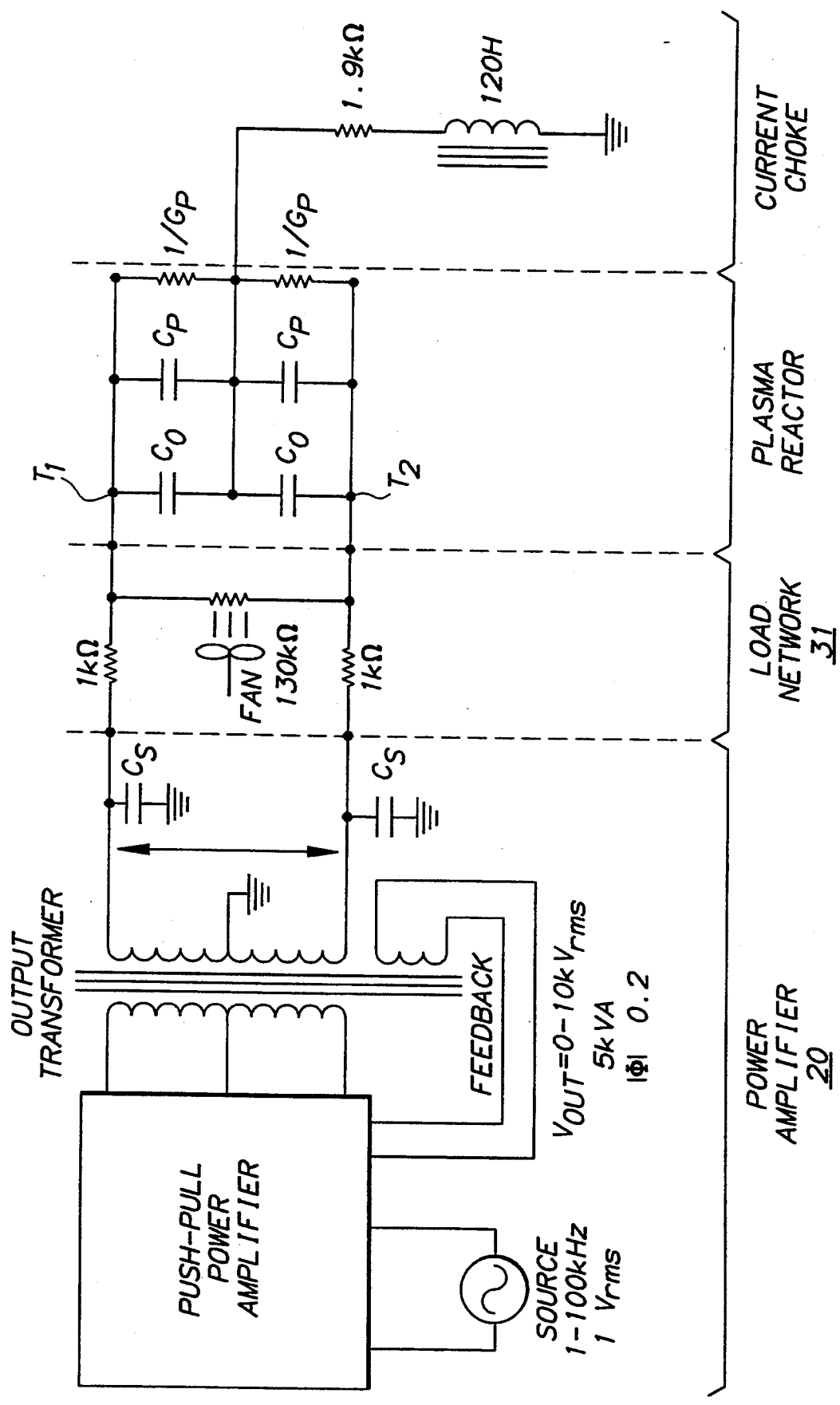
FIG. 2 is an impedance matching network distinctively suitable for powering the present invention.

To broaden the range of operating frequency and other parameters over which the desirable uniform (as opposed to filamentary) glow discharge occurs, an impedance matching network, one embodiment of which is illustrated schematically by FIG. 2, is added to the power circuit for charging the electrodes 10. The parameters of this matching network are adjusted for the most stable, uniform operation of the glow discharge. This condition can occur when the reactive power of the plasma reactor is minimized.

Figure 3:
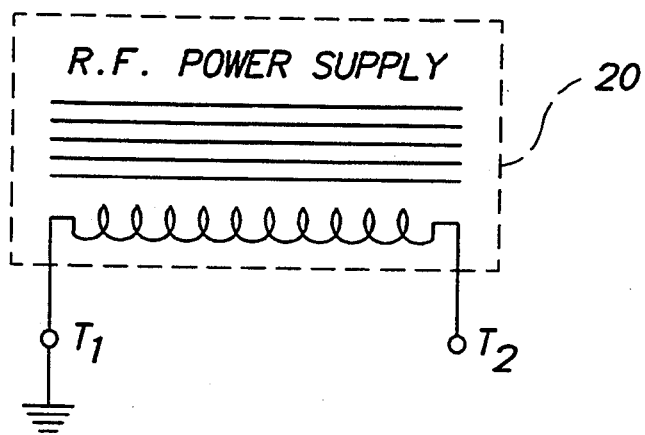
FIG. 3, 4 and 5 are representative alternative power supply output stage circuits.
Figure 4:
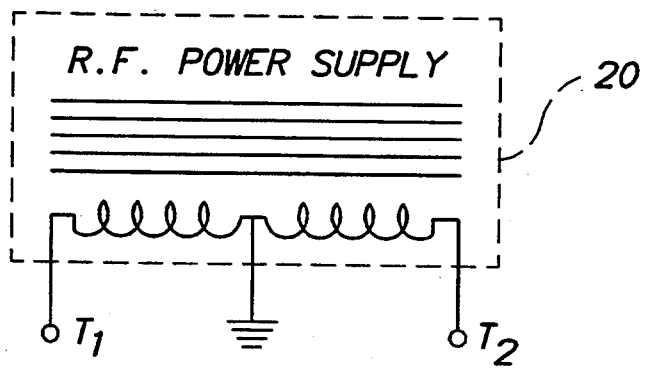
Figure 5:
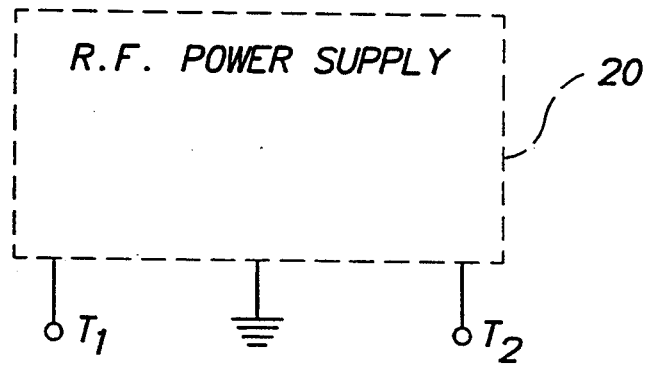

FIGS. 3 through 5 represent alternative power supply options having respective attractions. FIGS. 3 corresponds to a configuration wherein the bottom electrode terminal $T_1$ is connected to ground potential and the top terminal $T_2$ is charged at the full working potential. FIGS. 4 and 5 are electrical equivalents wherein the $T_1$ and $T_2$ voltages are 180° out of phase but at only half the maximum potential. FIG. 4 represents a grounded center tap transformer whereas FIG. 5 represents a solid state power circuit embodiment.

Figure 6:
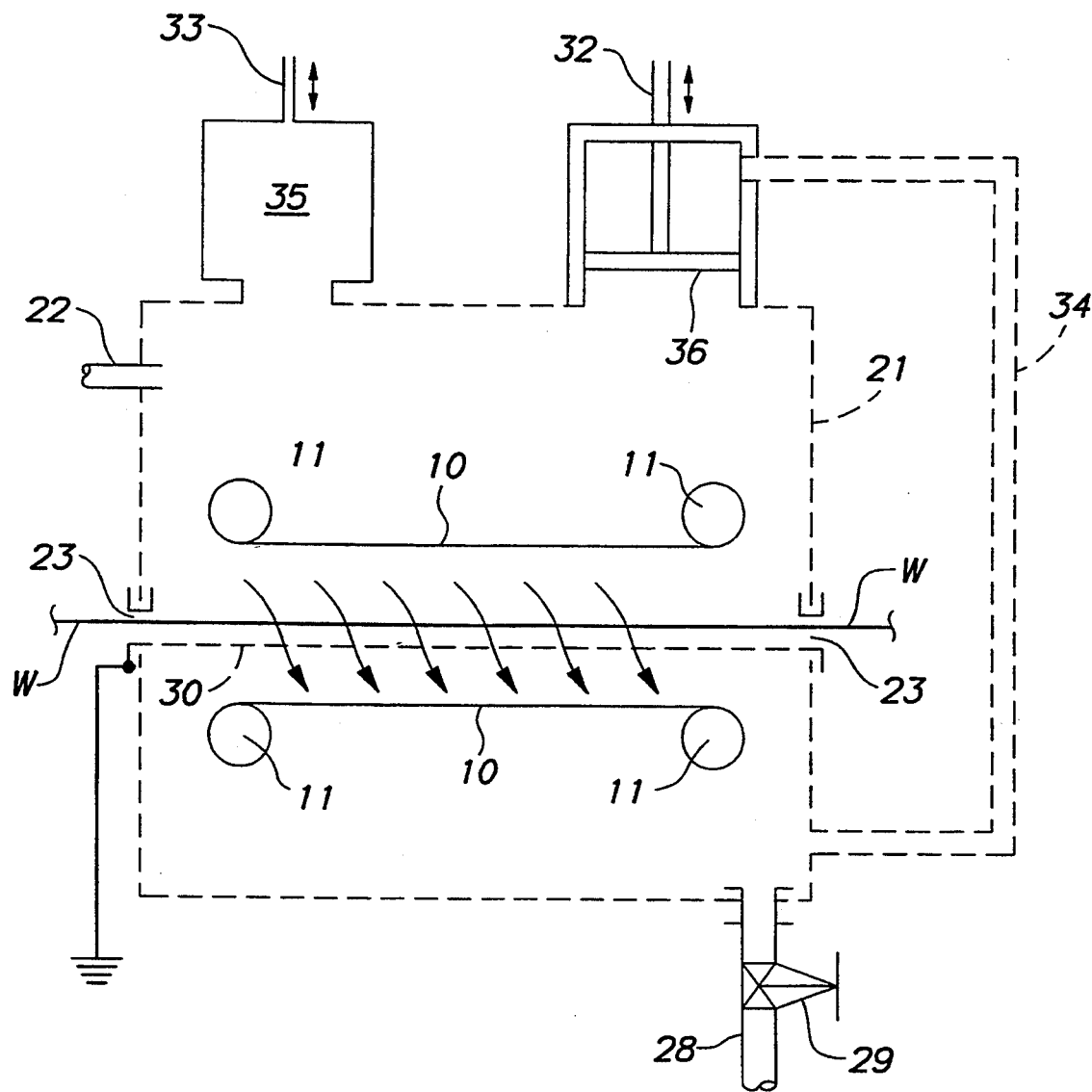
FIG. 6 schematically represents an alternative embodiment of the invention.

Shown in FIG. 6 are two optional embodiments, the functions of which are to drive a reciprocating gas flow containing active species from the plasma back and forth through the web W. This can be accomplished either by a bellows 35 actuated by a reciprocating shaft 33, or by a piston 36 activated by a reciprocating shaft 32. The change in volume of the upper chamber will give rise to a periodic reversal of the pressure differential across the web W, hence, a periodic reversal of the gas flow. As an alternative embodiment, a passageway from behind the piston can be connected to the lower chamber as shown in the dashed line piping 34.

The FIG. 6 embodiment of the invention provides an electrically grounded screen 30 to support the web W as it is drawn between the opposite material flow slits 23. This configuration attenuates an accumulated electrical charge on the web and also structurally supports the traveling fabric web as a pressure differential membrane between an upper, gas inlet chamber and a lower, vent chamber. This swept flow differential assures an internal saturation of the web W by the gas containing active species from the plasma.

Electric fields employed in a one atmosphere, uniform glow discharge plasma reactor are only a few kilovolts per centimeter, values which, if D. C., would usually be too low to electrically break down the background gas. Gases such as helium and air will break down under such low electric fields, however, if the positive ion population is trapped between the two parallel or uniformly spaced electrodes, this greatly increasing their lifetime in the plasma, while at the same time the electrons are free to travel to the insulated electrode plates where they recombine or build up a surface charge. The most desirable uniform one atmosphere glow discharge plasma is therefore created when the applied frequency of the RF electric field is high enough to trap the ions between the median screen and an electrode plate, but not so high that the electrons are also trapped during a half cycle of the R. F. voltage. The electrons may be trapped by bipolar electrostatic forces.

If the RF frequency is so low that both the ions and the electrons can reach the boundaries and recombine, the particle lifetimes will be short and the plasma will either not initiate or form a few coarse filamentary discharges between the plates. If the applied frequency is in a narrow band in which the ions oscillate between the median screen and an electrode plate, they do not have time to reach either boundary during a half period of oscillation and be carried for long times. If the more mobile electrons are still able to leave the plasma volume and impinge on the boundary surfaces, then the desirable uniform plasma is produced. If the applied RF frequency is still higher so that both electrons and ions are trapped in the discharge, then the discharge forms a filamentary plasma.

Figure 7:
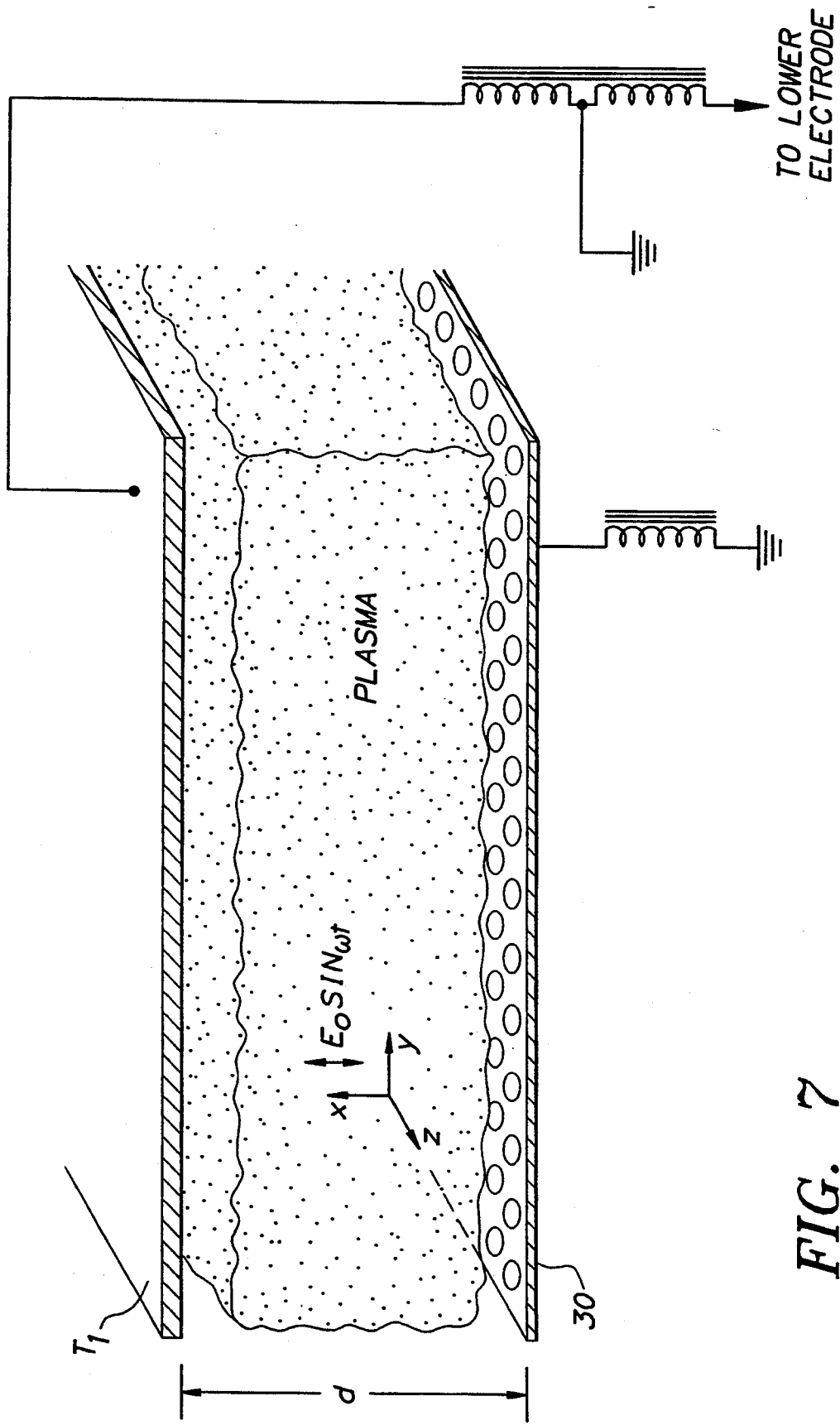
FIG. 7 schematically represents the upper chamber of a one atmosphere glow discharge plasma reactor having a median grid plate.

Without limiting our invention to any particular theory, we are disposed to a relationship between the electrode spacing, the RMS electrode voltage, and the applied frequency which results in trapping ions but not electrons between the two plates, and produces the desired uniform one atmosphere glow discharge plasma. On FIG. 7 is a schematic of the upper chamber of the one atmosphere glow discharge plasma reactor. The lower boundary of this space is the midplane screen or base, the floating potential of which should remain near ground if the RF power supply output is connected as a push-pull circuit to the two electrodes with a grounded center tap. In the data reported herein, the median screen was grounded through an inductive current choke. In the configuration of FIG. 7, a Cartesian coordinate system is applied as shown, with the applied electric field in the x-direction. The maximum amplitude of the electric field between the grounded median screen and the upper electrode is $E_o$, and the separation of the screen from the electrodes is the distance d. The median screen, with an exposed sample on it, is assumed not to allow ions through the median plane from the upper chamber to the lower, or vice-versa.

The electric field between the electrodes shown on FIG. 7 is given by $$E = (E_o \sin \omega t, 0, 0). \tag{1}$$

It is assumed that the one atmosphere glow discharge operates in a magnetic field free plasma. The equation of motion for the ions or electrons between the two plates is given by a Lorentzian model, in which the electrons and ions collide only with the neutral background gas and, on each collision, give up all the energy they acquired from the RF electric field since the last collision with the neutral gas. The equation of motion for the ions or electrons in the Lorentzian model is given by $$F = ms = -mv_c v - eE, \tag{2}$$

where the first term on the right hand side is the Lorentzian collision term, according to which the momentum $mv$ is lost with each collision that occurs with a collision frequency $v_c$. The x component of Eq. 2 is given by $$m \frac{d^2 x}{dt^2} + m v_c \frac{dx}{dt} = eE_o \sin \omega t, \tag{3}$$

where the electric field E from Eq. 1 has been substituted into the right hand side of Eq. 2. The general solution to Eq. 3 is $$x = C_1 \sin \omega t = C_2 \cos \omega t, \tag{4}$$

where the constants $C_1$ and $C_2$ are given by $$C_1 = -\frac{eE_o}{m} \frac{1}{(\omega^2 + v_c^2)}, \tag{5}$$

and $$C_2 = -\frac{v_c eE_o}{\omega m} \frac{1}{(\omega^2 + v_c^2)} \tag{6}$$

The one atmosphere helium glow discharge is operated at frequencies between $\omega/2\pi = 1$ and 30 KHz, where, for helium at one atmosphere, $$v_{ci} \approx 6.8 \times 10^9 \text{ ion collisions/sec.}, \tag{7a}$$

and $$v_{ce} \approx 1.8 \times 10^{12} \text{ electron coll./sec.} \tag{7b}$$

The collision frequency for ions and electrons given by Eqs. 7a and 7b is much greater than the RF frequency, $V_c >> \omega$. The relation $v_c >> \omega$ for ions and electrons, implies that $C_2$ is much greater than the constant $C_1$, or $$C_2 \approx \frac{eE_o}{m\omega v_c} >> C_1 \tag{8}$$

The time dependent position of an ion or an electron in the electric field between the plates is given by substituting Eq. 8 into Eq. 4, to obtain $$x(t) \approx -\frac{eE_o}{m\omega v_c} \cos \omega t. \tag{9}$$

The RMS displacement of the ion or electron during a half cycle is given by $$x_{rms} = \frac{2}{\pi} \frac{eE_o}{m\omega v_c} \text{ meters.} \quad (10)$$

If $V_o$ is the driving frequency, in Hertz, then the radian RF frequency is given by $$\omega = 2\pi v_o, \quad (11)$$

and the maximum electric field between the plates can be approximated by the maximum voltage $V_o$ appearing between them, $$E_o = \frac{V_o}{d} = \frac{\pi V_{rms}}{2d}. \quad (12)$$

If the charge in question moves across the discharge width from the median plane to one of the electrode plates during one full cycle, then we may write $$x_{rms} \leq \frac{d}{2}. \quad (13)$$

Equation 13 states that the RMS displacement of the particle has to be less than half the clear spacing in order to have a buildup of positive charge between the plates. In the geometry shown in FIG. 7, the distance d is identified with the distance between the grounded median screen and the energized electrode. Substituting Eqs. 11 to 13 into Eq. 10 yields the relationship $$\frac{d}{2} \approx \frac{eV_{rms}}{2\pi m v_o v_c d}. \quad (14)$$

If we now solve for the critical frequency $v_o$ above which charge buildup should occur in the plasma volume, we have $$v_o \approx \frac{eV_{rms}}{\pi m v_c d^2} \text{ Hz.} \quad (15)$$

In Eq. 15, the collision frequency va is given by Eqs. 7a or 7b for ions or electrons, respectively, at one atmosphere, and the RMS voltage is that which bounds the upper and lower limit of the uniform discharge regime.

The range of parameters over which we have operated a one atmosphere, uniform glow discharge plasma reactor is given in Table I. The nominal pressure at which this discharge has been operated is one atmosphere. The variation of several torr shown in Table I is not intended to represent the day-to-day fluctuations of barometric pressure, but the pressure differential across the midplane screen which is intended to drive active species from the upper plasma through the fabric being exposed. The RMS power shown in Table I is the net power delivered to the plasma, less the reactive power which does not appear in the plasma. The total volume of plasma between the two electrode plates is given by $$S = 0.93 \ d(cm) \text{ liters,} \quad (16)$$

where d is the separation of a plate from the median screen in centimeters.

The power densities shown in Table I are far below those of electrical arcs or plasma torches, but also are several orders of magnitude higher than the power densities associated with some other forms of plasma treatment such as corona discharges. The power densities of the one atmosphere glow discharge plasma are generally low enough not to damage exposed fabrics, but are also enough higher than coronal plasmas used for surface treatment that they should provide far more active species than the latter. The plasma parameters, such as electron kinetic temperature and number density are somewhat speculative at this early stage in the development of our invention. A few results from probing the plasma midplane with a floating Langmuir probe indicates that the plasma, without grounding the midplane screen, will float to positive potentials of several hundred volts. The ion kinetic temperatures are very likely close to that of the room temperature atoms with which they frequently collide at these high pressures; the electrons apparently remain numerous and energetic enough to excite the neutral background atoms, hence making this a glow discharge. The existence of excited states which emit visible photons implies that the electron population has a kinetic temperature of at least an electron volt. The diagnostic difficulties of measuring plasma parameters at this high pressure are very severe, since ordinary Langmuir probing technique cannot be applied due to the short mean free paths of the electrons compared to a Debye distance. Electron number densities, however, may be measured by microwave interferometric techniques.

TABLE I

| OPERATING CHARACTERISTICS OF THE ONE ATMOSPHERE GLOW DISCHARGE PLASMA REACTOR |
| --- |
| working gas = He, He + 1–7% $O_2$, Ar, Ar + He, Ar + 1–7% $O_2$, and atmospheric air |
| frequency = 1 KHz to 100 KHz |
| voltage = 1.5–9.5 kV$_{rms}$ plate to plate |
| electrode gap d = 0.8–3.2 cm |
| pressure = 760 +15, −5 torr |
| RMS power = 10 watts to 150 watts |
| power density = 4–120 mW/cm$^3$ |
| plasma volume = 0.7–3.1 liters |

Figure 8A:
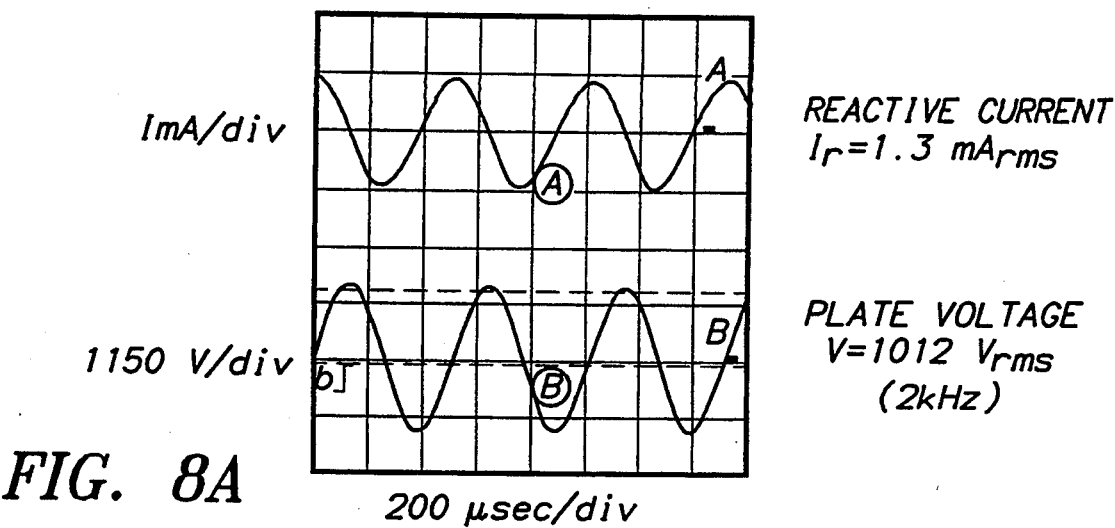
FIG. 8 represents a graph of voltage, current and power waveforms for a uniform glow discharge plasma.
Figure 8B:
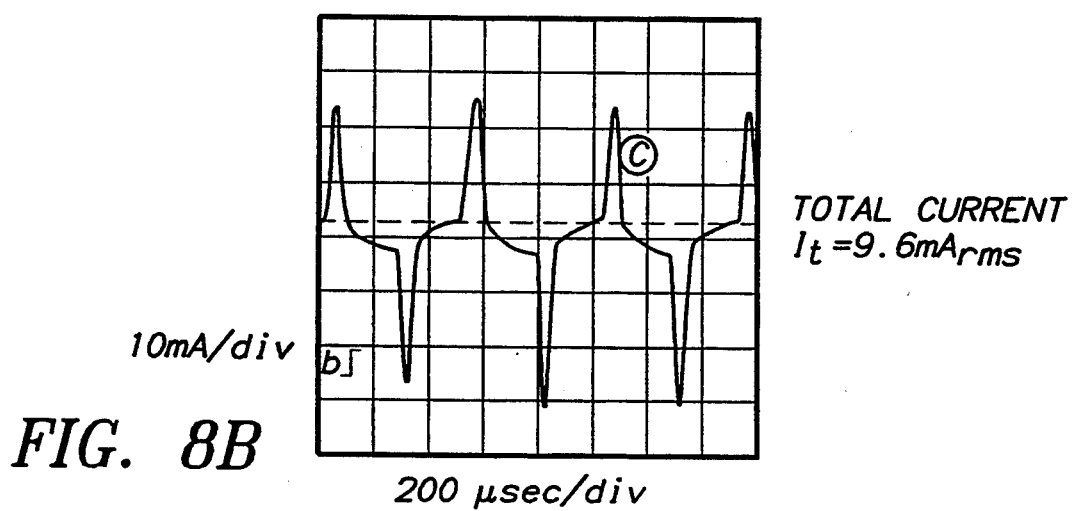
Figure 8C:
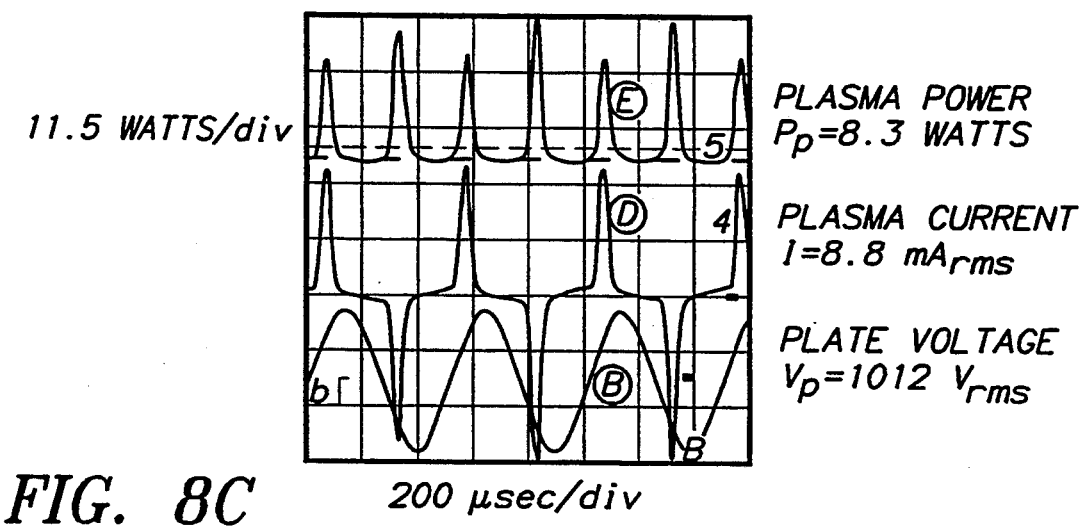
Figure 9A:
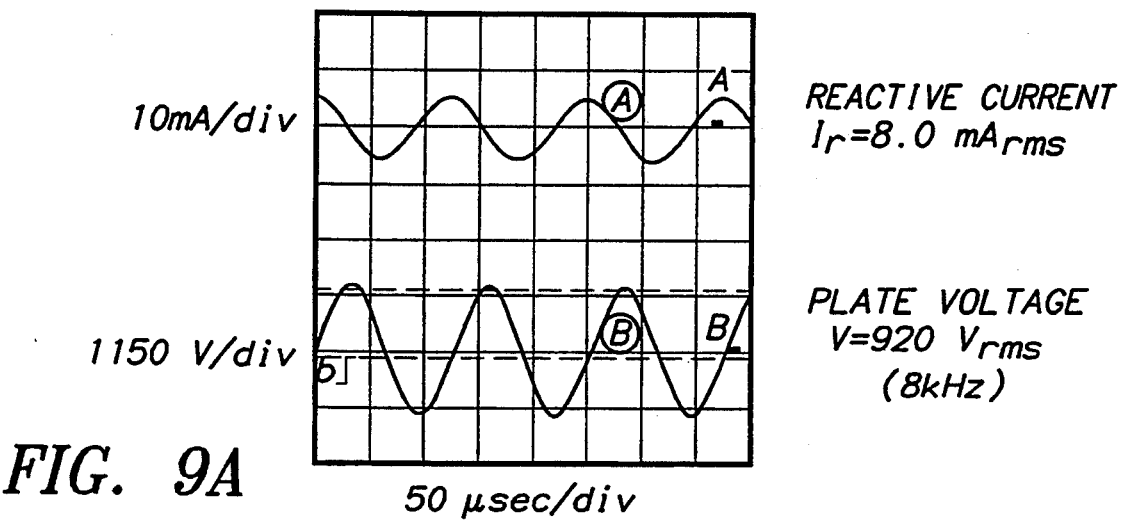
FIG. 9 represents a graph of voltage, current and power waveforms for a filamentary discharge plasma.
Figure 9B:
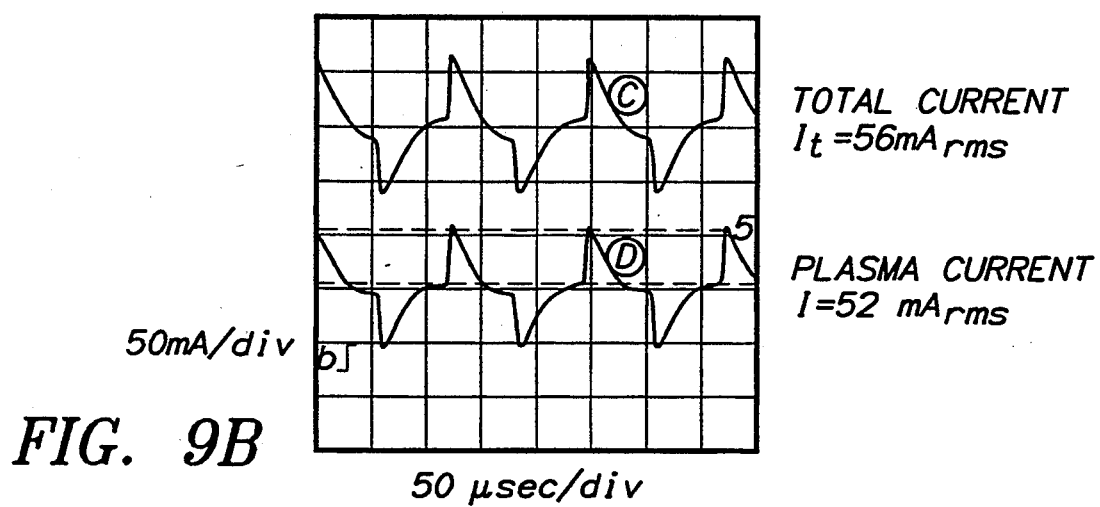
Figure 9C:
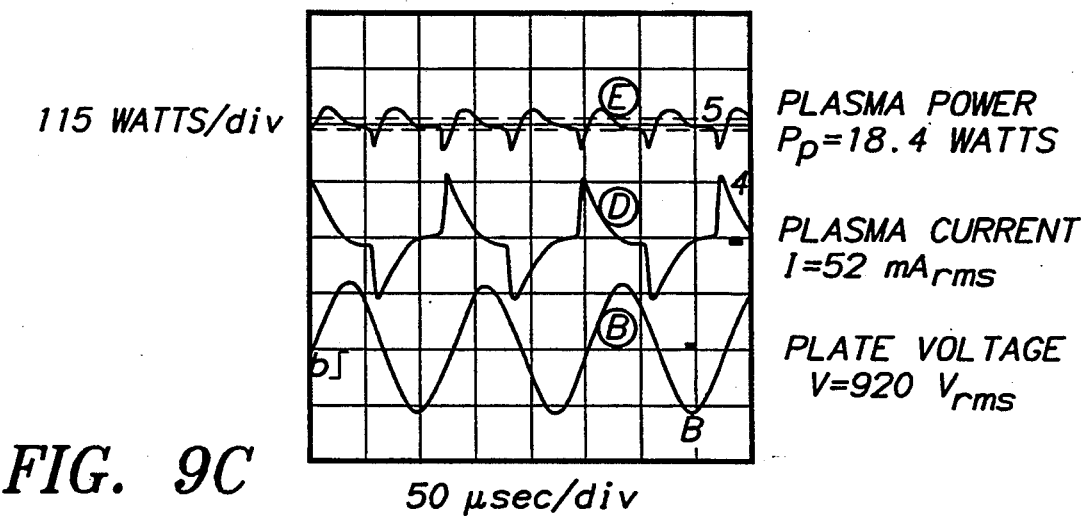

On FIGS. 8 and 9 are shown two waveforms of voltage and current taken in helium at the same electrode separation and gas flow conditions, but at two different frequencies. FIG. 8 was taken in the uniform glow discharge regime at a frequency of 2.0 kHz, and FIG. 9 was taken in the filamentary discharge regime at a frequency above the uniform plasma operating band at 8.0 kHz. The high output impedance of our RF power supply results in a voltage waveform (trace B) that is very close to sinusoidal. The reactive current waveform (trace C) is interrupted by a breakdown of the plasma twice each cycle, once when the voltage is positive, and once when the voltage is negative. Trace A shows the reactive current waveform at the same voltage and operating conditions, but in air, rather than helium. There was no perceptible plasma present in air under these conditions, and the power is completely reactive. This purely reactive current of trace A was subtracted from the total plasma current in trace C, to yield trace D. The instantaneous power deposited in the plasma (trace E) is found by multiplying the excess plasma current above the reactive current (trace D) by the voltage at that point (trace B). The average power is found by integrating over the duration of the pulses shown, and dividing by this duration. It is in this manner that the power and power density into the plasma were calculated for these highly nonsinusoidal current waveforms. FIGS. 8 for the uniform discharge and 9 for the filamentary discharge show characteristically different power waveforms in trace E; this is a method of distinguishing the uniform from the filamentary discharge.

Figure 10:
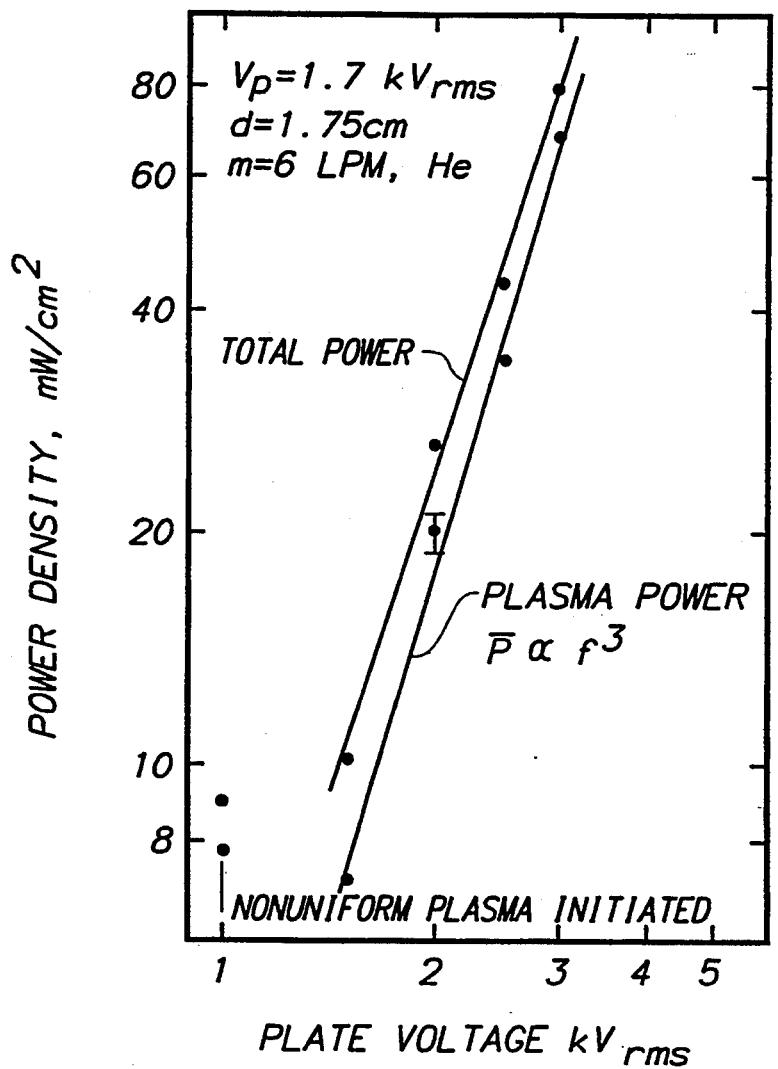
FIG. 10 is a log-log graph of total and plasma power density in milliwatts per cubic centimeter, as functions of RMS voltage applied to the electrodes.
Figure 11:
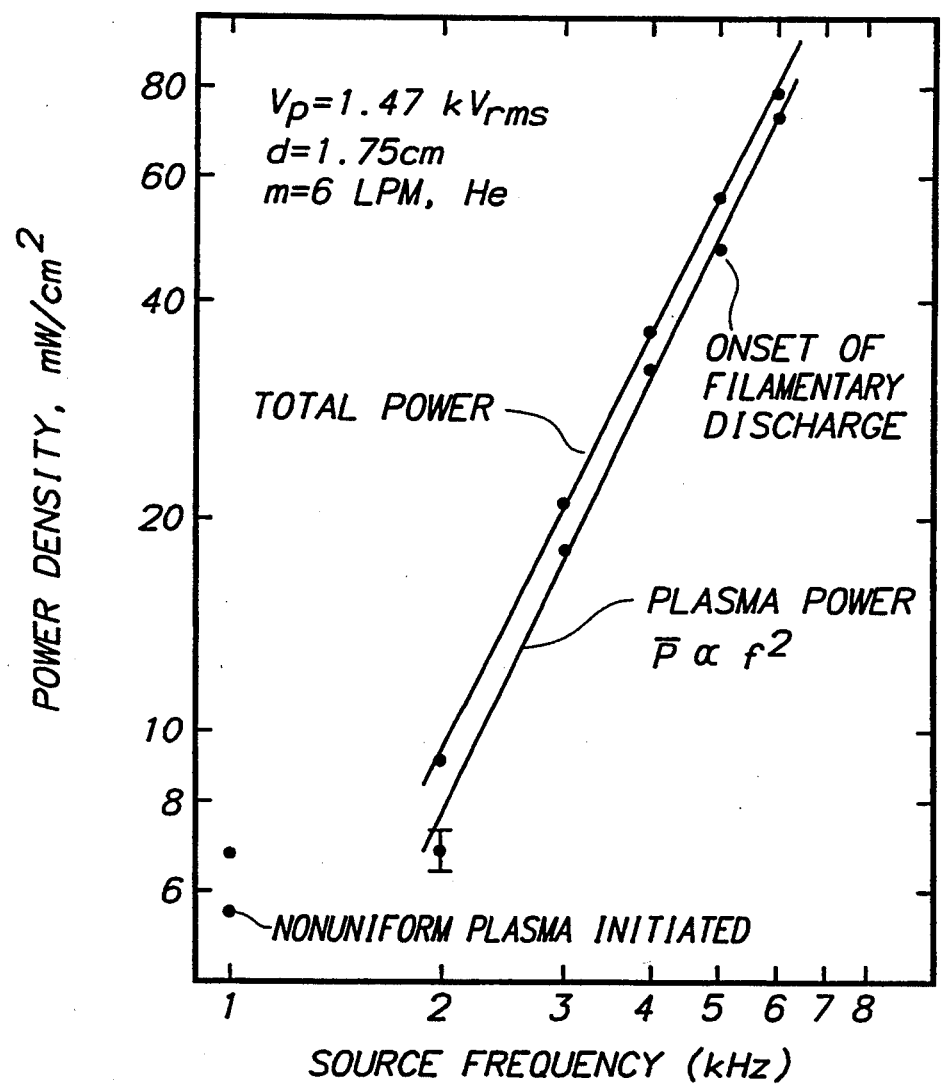
FIG. 11 is a log-log graph of total and plasma power density in milliwatts per cubic centimeter, as functions of R. F. frequency.

The plasma power is of interest because it is proportional to the production rate of active species in the plasma; the reactive power is significant because it determines the required power handling rating of the plasma power supply and associated equipment. The total power is the sum of plasma and reactive power. On FIG. 10 is shown a log-log plot of the plasma and total power density in milliwatts per cubic centimeter, as functions of the RMS voltage applied to the parallel plates. The active plasma volume in FIG. 10 was 1.63 liters, with a separation between the median screen and each plate of d=1.75 centimeters in a plasma of helium gas. On FIG. 11 is a similar presentation of the power density plotted on log-log coordinates as a function of the frequency. The approximate bound of the uniform plasma discharge regime is shown by the arrow. These data were taken in helium gas for the same plasma volume and electrode separation as FIG. 10.

EXAMPLE 1

Figure 12:
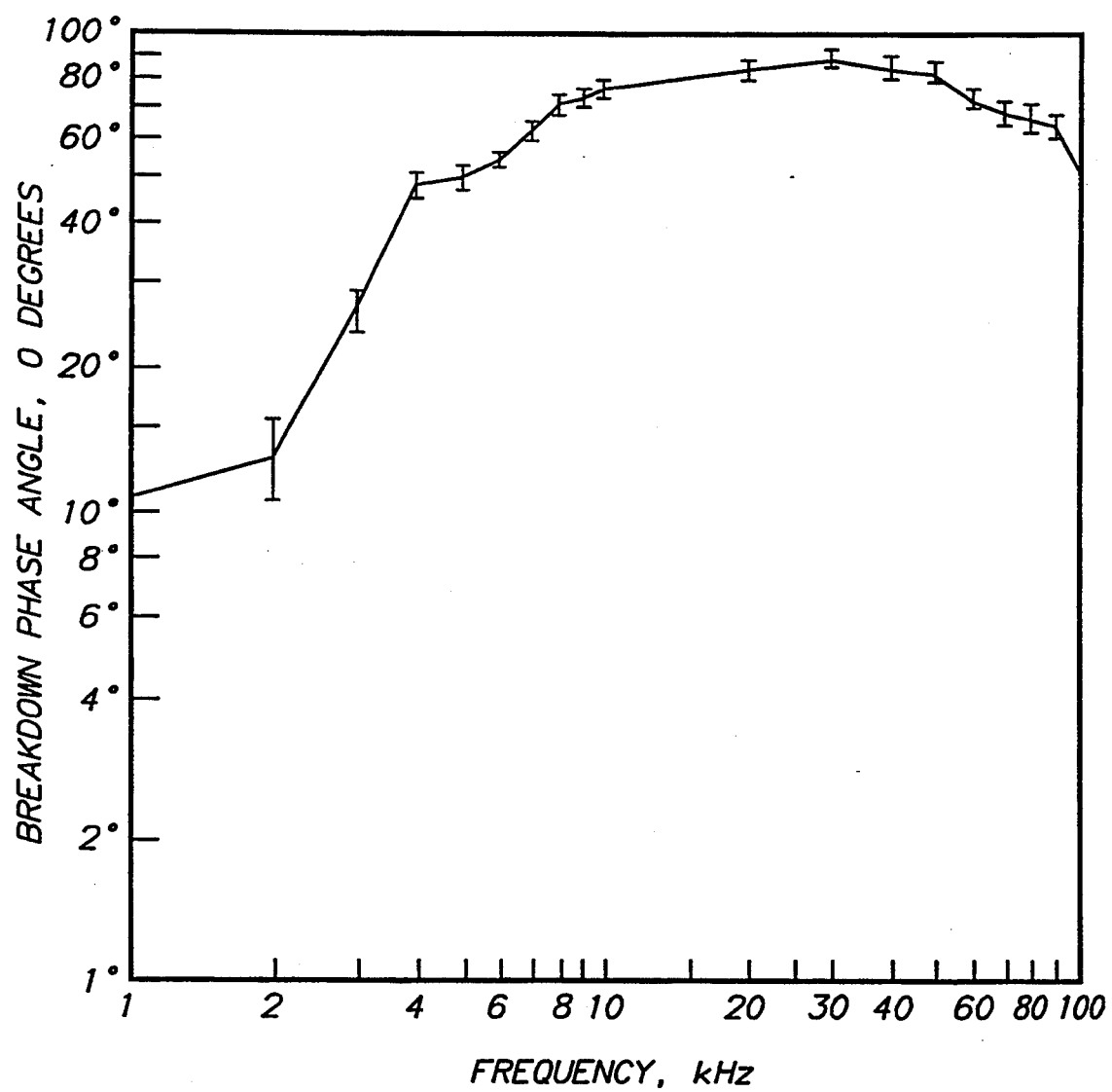
FIG. 12 is a graph of amplifier frequency and corresponding breakdown current phase angles respective to a particular operating example of the invention.
Figure 13:
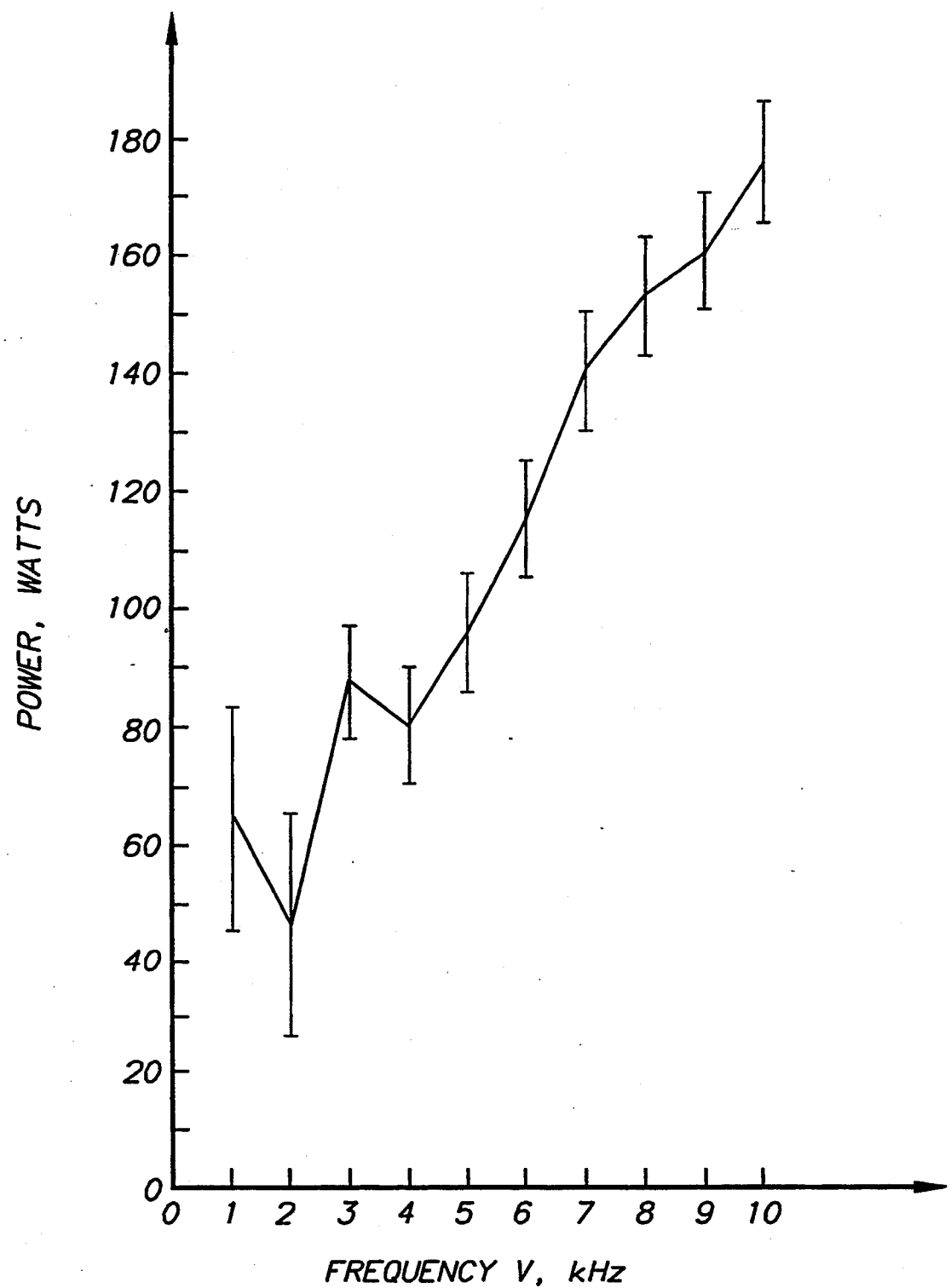
FIG. 13 is a graph of amplifier frequency and corresponding power consumption respective to a particular operating example of the invention.

In a first operational example of the invention, the FIG. 1 described physical apparatus sustained a glow discharge plasma in one atmosphere of helium at standard temperature with a separation distance s of 3.0 cm between plates 10. The plates were energized with a 4.4 KV rms working potential. Holding these parameters constant, R. F. frequency was increased as an independent variable. As the dependent variable, FIG. 12 charts the corresponding breakdown current phase angle as determined relative to the voltage waveform node. Similarly, FIG. 13 charts the total power, including reactive and plasma input power required to sustain the plasma at the respective R. F. frequencies.

EXAMPLE 2

In a second operational example of the invention, the FIG. 1 described physical apparatus is used to sustain a glow discharge plasma in one atmosphere of helium at standard temperature with a separation distance s of 1.0 cm between plates 10. In this example, the R. F. frequency was held constant at 30 KHz while plate potential was manipulated as the independent variable and current breakdown phase angle, Θ, (Table 2) and total power, P, (Table 3) measured as dependent variables.

TABLE 2

| V(KV) | 1 | 1.5 | 2 | 2.5 | 3 | 3.5 |
|---|---|---|---|---|---|---|
| θ(deg) | 28 | 40 | 61 | 46 | 65 | 76.5 |

TABLE 3

| V(KV) | 1 | 1.5 | 2 | 2.5 | 3 | 3.5 |
|---|---|---|---|---|---|---|
| P(W) | 7 | 13 | 22 | 57 | 50 | 44.9 |

EXAMPLE 3

A third operational example of the invention included a one atmosphere environment of helium between a 1 cm separation distance s between plate electrodes 10 charged at 1.5 KV rms potential. The R. F. frequency was manipulated as the independent variable. As a measured dependent variable, Table 4 reports the corresponding phase angle Θ of breakdown current. The measured dependent variable of Table 5 reports the corresponding total power consumption data.

TABLE 4

| f(KHz) | 10 | 20 | 30 | 40 | 50 | 60 | 70 | 80 | 90 | 100 |
|---|---|---|---|---|---|---|---|---|---|---|
| θ(deg) | 43 | 32 | 43 | 52 | 54 | 61 | 60 | 56 | 45 | 22.5 |

TABLE 5

| f(KHz) | 10 | 20 | 30 | 40 | 50 | 60 | 70 | 80 | 90 | 100 |
|---|---|---|---|---|---|---|---|---|---|---|
| P(W) | 5 | 8 | 11 | 19 | 35 | 43 | 47 | 57 | 89 | 124 |

EXAMPLE 4

The largest volume helium plasma of 3.1 liters was achieved with the above described apparatus at a 3.7 cm plate separation having a 5 KV rms potential at an R. F. frequency of 4 KHz.

Meltblown webs formed from nylon, poly(ethylene terephthalate), polypropylene and polyethylene have been processed by exposure to the glow discharge plasma described herein to produce desired material characteristics, increased wettability and re-wettability.

Wettability of a material is objectively measured by either or both of two tests including (a) the angle of a water bead supported on the material surface and (b) the time required to wick along a predetermined material length.

By such tests, it was determined that polypropylene, nylon, polyester and polyethylene film experienced a significant wettability and re-wettability improvement after a 2.5 minute plasma exposure as evidenced by a greatly reduced bead angle.

A poly(ethylene terephthalate) web, after 2.5 minutes of glow discharge plasma exposure to a 5 KV, 4 KHz across a 4.5 cm plate separation, experienced a 0° surface bead angle and a 37.37 second wicking rate determined by the INDA standard absorption test. Prior to plasma exposure, the web had a large surface bead angle and no wicking capacity.

Similarly, after only 60 seconds of exposure to the same plasma, a nylon web, having a high surface bead angle and no wicking capacity enjoyed a 0° surface bead angle and a 16.61 second wicking rate (INDA standard test) upon wetting and re-wetting.

In another test set, two different meltblown webs Poly(ethylene terephthalate) and polypropylene (PET and PP), were treated by the one atmosphere glow discharge plasma with helium or helium plus active gases as the working gas for a treating time period from half minute to two minutes. The power supply voltage was from 1,000 V$_{rms}$ to 4,000 V$_{rms}$ and the frequency was from 1 kHz to 100 kHz. The webs had a fiber size of 2 to 2.5 microns, a pore size of 20–25 microns, and a porosity of 90%. Table 6 lists some initial results from these treatments.

Wettability was justified by contact angle, wickability, and wetout of the liquid through web thickness and on the web surface. Wickability was measured according to INDA standard (1st 10.1-92), in which time was measured for the liquid (double D's water) to rise 2.4 cm high. Physical fiber surface change was analyzed by photomicrographs taken using the ETEC Auto Scan electron microscope for a magnification of 2,000× to 4,000×.

TABLE 6

| Sample | Treating Conditions Time(s) | gases | kV$_{rms}$ | Wettability Contact Angle | Wicking Rate(s) | Thickness Wettability | Surface Wettability |
|---|---|---|---|---|---|---|---|
| PP 0.35 oz | 60 | He, O$_2$ | 3.5 | reduced | not sig. | 90% | good |
| PP 0.35 oz | 60 | He, O$_2$ | 3.0 | unchanged | no | 75% | increased |
| PET 1 oz | 90 | He | 2.3 | 0 | 31.74 | good | good |

Although expansive data is not presently available, it is to be noted that a uniform glow discharge plasma has been sustained by the FIG. 1 apparatus with a one atmosphere ambient air environment and an 8 kV/cm electric field.

Having fully disclosed our invention and the presently preferred embodiments and best modes of practice,

We claim:

1. A method for improving the surface characteristics of a web comprising the steps of generating in a gas maintained at about atmospheric pressure a sustained, uniform glow discharge plasma having active species between a pair of spaced electrodes, wherein said generating step includes energizing said electrodes at a voltage of at least about 1 kV rms at frequencies of about 1 to 100 kHz, and positioning said web between said electrodes and within said plasma for a period of time and pressure differentially driving the active species through said web.

2. A method as described by claim 1 wherein a volume defined by the space between said electrodes is charged with said gas.

3. A method as described by claim 2 wherein said gas is helium.

4. A method as described by claim 2 wherein said gas is a mixture of helium and air.

5. A method as described by claim 2 wherein said gas is argon.

6. A method as described by claim 2 wherein said gas is a mixture of argon and air.

7. A method as described by claim 2 wherein said gas is a mixture of argon and helium.

8. A method as described by claim 2 wherein said gas is atmospheric air.

9. A method as described by claim 2 wherein said gas is nitrous oxide.

10. The method of claim 1 wherein said voltage is in the range of about 1 kV to 5 kV rms.

11. The method of claim 1 wherein said voltage is in the range of about 1.5 kv to 9.5 kV 12. The method of claim 2 wherein said gas is a noble gas.

* * * * *